United States Patent [19]

Hattler

[11] Patent Number: 5,122,113
[45] Date of Patent: Jun. 16, 1992

[54] INFLATABLE PERCUTANEOUS OXYGENATOR

[76] Inventor: Brack G. Hattler, 5226 Westminster Pl., Pittsburgh, Pa. 15232

[21] Appl. No.: 676,262

[22] Filed: Mar. 27, 1991

[51] Int. Cl.$^5$ ............................................. A61M 37/00
[52] U.S. Cl. ....................................... 604/26; 604/49; 604/96; 604/101; 604/4; 128/DIG. 3; 623/3
[58] Field of Search ................................ 128/DIG. 3; 261/DIG. 28; 604/23–28, 49, 43, 96, 99, 101; 606/192, 194–196; 623/1, 3, 9, 11, 12

[56] References Cited

U.S. PATENT DOCUMENTS

| | | | |
|---|---|---|---|
| 3,505,686 | 4/1970 | Bodell | 3/1 |
| 3,729,377 | 4/1973 | Leonard | 195/1.8 |
| 4,159,720 | 7/1979 | Burton | 128/260 |
| 4,346,006 | 8/1982 | Konn et al. | 210/321.4 |
| 4,576,590 | 3/1986 | Fiddian-Green | 604/26 |
| 4,583,969 | 4/1986 | Mortensen | 604/49 |
| 4,631,053 | 12/1986 | Taheri | 604/49 |
| 4,743,250 | 5/1988 | Kitagawa et al. | 623/1 |
| 4,793,350 | 12/1988 | Mar et al. | 604/96 |
| 4,821,722 | 4/1989 | Miller et al. | 604/96 |
| 4,850,958 | 7/1989 | Berry et al. | 604/26 |
| 4,911,689 | 3/1990 | Hattler | 604/26 |
| 4,986,809 | 1/1991 | Hattler et al. | 604/26 |
| 5,037,383 | 8/1991 | Vaslef et al. | 604/49 |

OTHER PUBLICATIONS

Tanishita et al., "Augmentation of Gas Transfer with Pulsatile Flow in the Coiled Tube Member Oxygenator Design", 26, Trans. Am. Soc. Artif. Intern. Organs, 561 (1980).

*Primary Examiner*—Stephen C. Pellegrino
*Assistant Examiner*—Michael Rafa

[57] ABSTRACT

An inflatable percutaneous oxygenator has an inflatable balloon suitable for insertion into a blood vessel. Oxygen is circulated through a number of gas-permeable passageways (such as hollow gas-permeable fibers) adjacent to the balloon surface to permit diffusion of oxygen and carbon dioxide between the blood vessel and the passageways. A pump is used to alternately expand and contract the balloon. This causes movement of the passageways within the blood vessel to minimize streaming or channeling of the blood flow around the oxygenator, maximizes turbulence in the blood stream, and therefore maximizes diffusion of gases. An external connector has lumens that supply a flow of oxygen to the passageways, exhaust gas from the passageways, and allow inflation and deflation of the balloon by the pump.

30 Claims, 4 Drawing Sheets

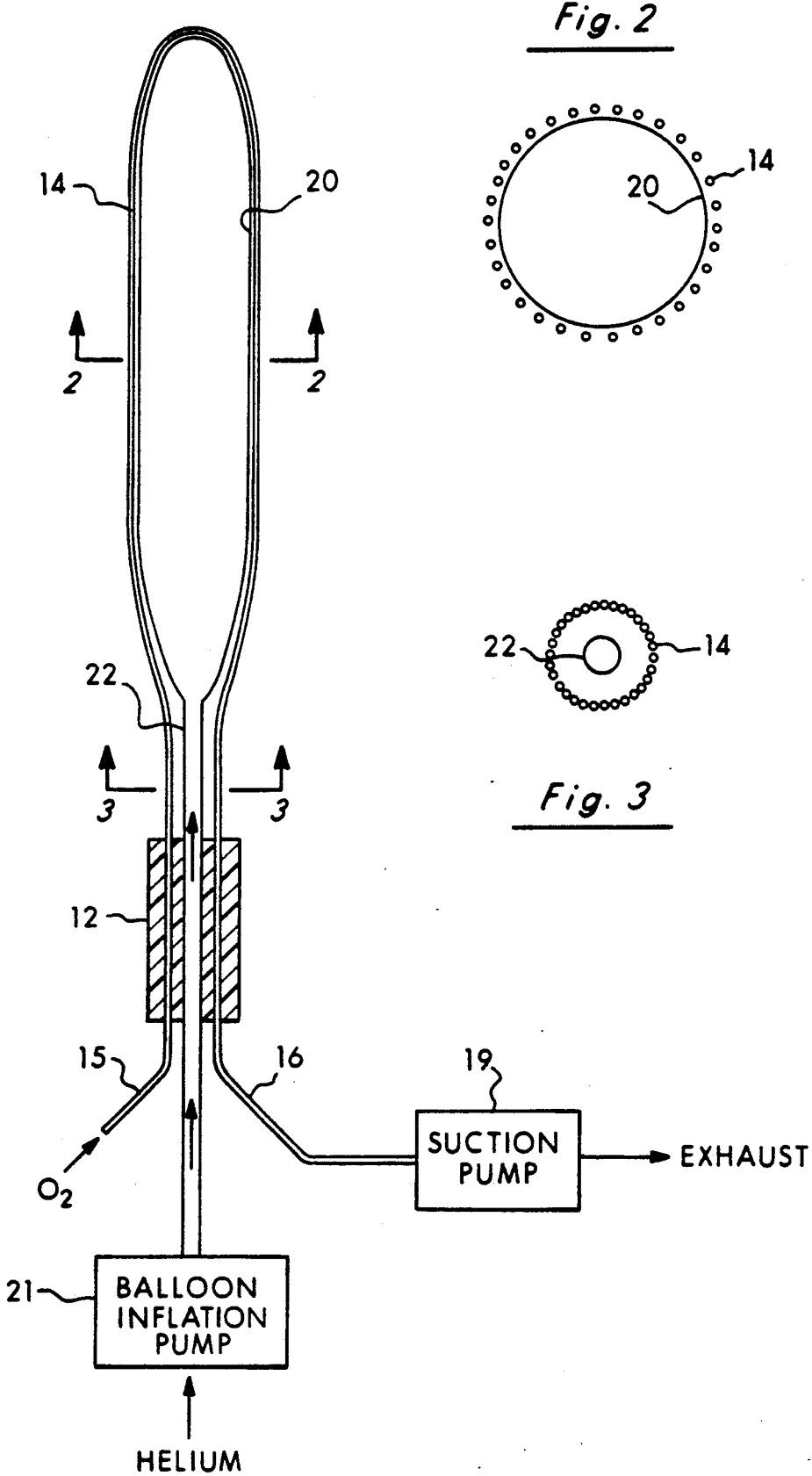
Fig. 1
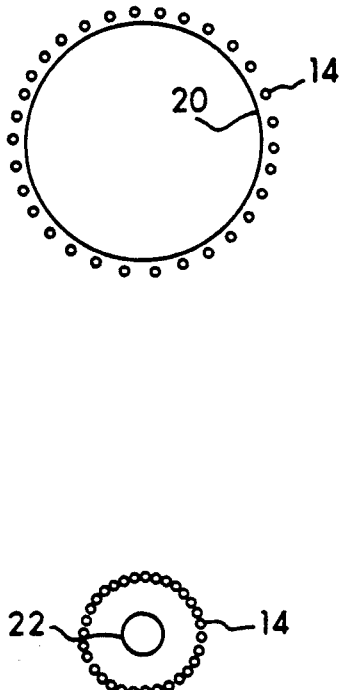
Fig. 2
Fig. 3

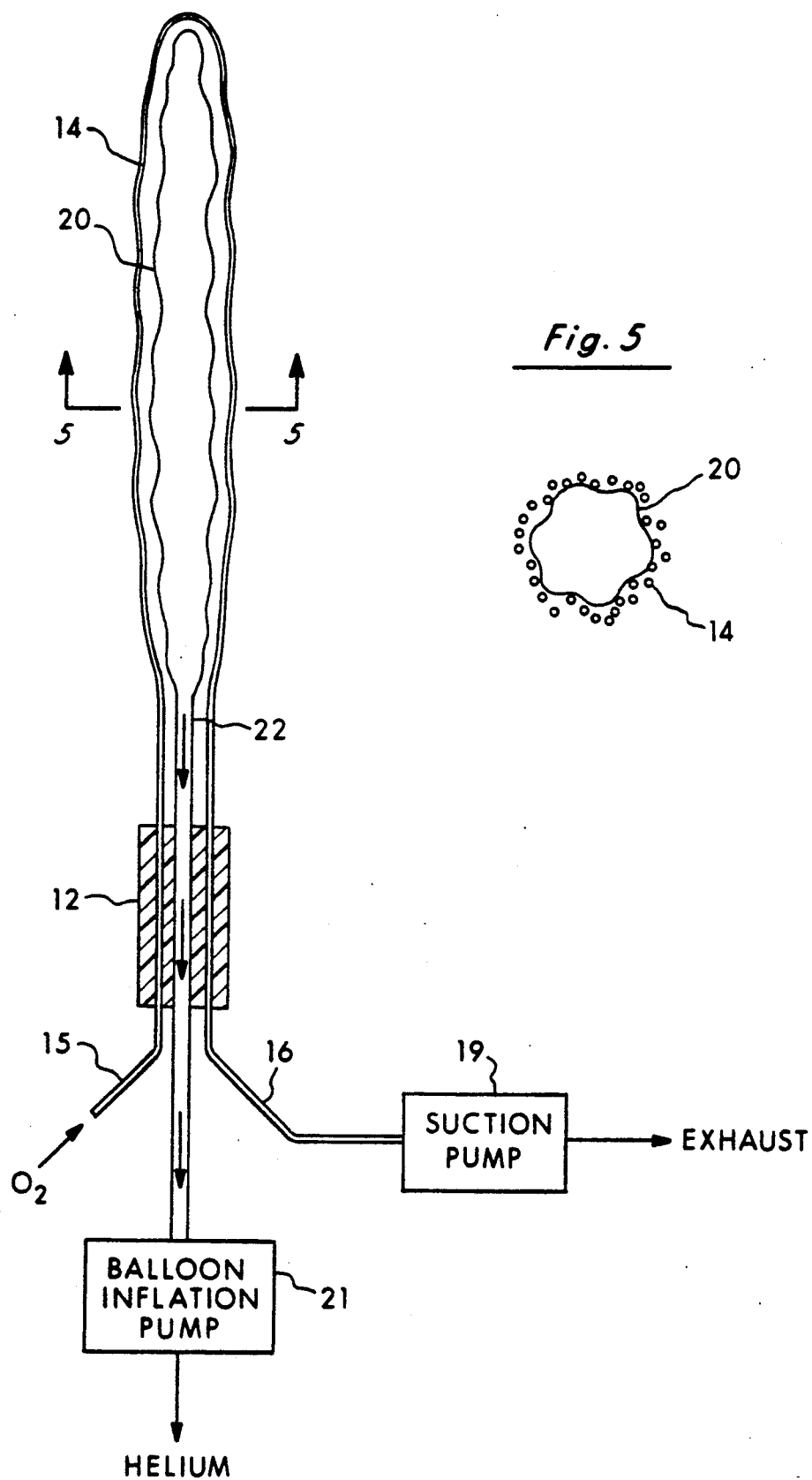

INFLATABLE PERCUTANEOUS OXYGENATOR

BACKGROUND OF THE INVENTION

1. Field of the Invention

The present invention relates generally to the field of oxygenators used to increase the oxygen level in a patient's blood. More particularly, the present invention involves a percutaneous oxygenator that can be positioned within a patient's body (e.g. in the inferior vena cava, superior vena cava, the right atrium of the heart, or any combination thereof) and then repeatedly inflated and deflated to minimize streaming of the blood flow around the oxygenator, and thereby maximize the cross-diffusion of oxygen and carbon dioxide.

2. Statement of the Problem

Many types of blood oxygenators are well known in the art. For example, during open heart surgery, the patient is interconnected with an external oxygenator, commonly known as a heart-lung machine, which introduces oxygen into the blood system. Most types of oxygenators use a gas-permeable membrane. Blood flows along one side of the membrane, and oxygen is supplied to the other side of the membrane. Given a sufficient pressure gradient between the oxygen supply and the blood, the oxygen will diffuse through the membrane and into the blood. In addition, carbon dioxide will tend to diffuse from the blood through the membrane.

In other situations, a smaller, implantable oxygenator may be sufficient to adequately supplement the patient's cardiopulmonary function by marginally increasing the oxygen content of the patient's blood. For example, patients suffering from emphysema, pneumonia, congestive heart failure, or other chronic lung disease often have blood oxygen partial pressures of approximately 40 torr. A relatively small increase of 10% to 20% is generally sufficient to adequately maintain the patient. This is a particularly desirable alternative in that it avoids the need to intubate the patient in such cases. In addition, temporary use of this type of oxygenator is sufficient in many cases to tide the patient over an acute respiratory insult. Placing such patients on a conventional respirator is often the beginning of a progressive downhill spiral by damaging the patient's pulmonary tree and thereby causing greater dependence on the respirator.

The effective rate of diffusion in percutaneous oxygenators can be limited in some instances by the problem of "streaming" or "channeling", in which the blood stream establishes relatively stable patterns of flow around and through the oxygenator. Portions of the oxygenator are exposed to a relatively high velocity, turbulent flow of blood. These conditions tend to increase cross-diffusion of oxygen and carbon dioxide. However, other portions of the oxygenator are exposed to a low velocity, laminar flow of blood which reduces diffusion of gases. Those portions of the oxygenator immediately adjacent to the regions of high blood flow may continue to experience high rates of diffusion, but the remaining portions of the oxygenator tend to have relatively low diffusion rates. Thus, the overall diffusion rate of the oxygenator can be substantially diminished by streaming.

A number of devices and processes have been invented in the past relating to different types of oxygenators, including the following:

| Inventor | Patent No. | Issue Date |
| --- | --- | --- |
| Bodell | 3,505,686 | Apr. 14, 1970 |
| Burton | 4,159,720 | July 3, 1979 |
| Kopp, et al. | 4,346,006 | Aug. 24, 1982 |
| Mortensen | 4,583,969 | Apr. 22, 1986 |
| Taheri | 4,631,053 | Dec. 23, 1986 |
| Kitagawa, et al. | 4,743,250 | May 10, 1988 |
| Berry, et al. | 4,850,958 | July 25, 1989 |
| Hattler | 4,911,689 | Mar. 27, 1990 |
| Hattler, et al. | 4,986,809 | Jan. 22, 1991 |

Tanishita, et al., "Augmentation of Gas Transfer with Pulsatile Flow in the Coiled Tube Member Oxygenator Design", 26 Trans. Am. Soc. Artif. Intern. Organs 561 (1980).

Bodell demonstrates the general concept of using gas-permeable fibers to boost the oxygen level of blood. FIGS. 6 and 10 show two variations of this device intended for use inside the body of the patient. In the implantable embodiment of the Bodell device, a tubular casing serves as a shunt either from the pulmonary artery to the left atrium of the heart (FIG. 6), or more generally between an artery and a vein (FIG. 10). A multitude of parallel-connected capillary tubes are used to oxygenate and/or purify the blood circulating through the casing.

FIGS. 3–5 of the Mortensen patent show a transvenous oxygenator made of a plurality of small diameter gas-permeable tubes 32 connected to headers 34 and 36 at each end. However, the specific device disclosed by Mortensen has a significant disadvantage in that two incisions are required. The insertion process is also rather complex.

Taheri discloses a transvenous oxygenator having a single membrane 16 through which oxygen diffuses. The membrane is disposed within a sheath 18 and both are supported by a flexible wire 20.

Berry, et al., disclose an in vivo extrapulmonary blood gas exchange device having a bundle of elongated gas permeable tubes 12 bound at each end and enclosed within a respective air-tight proximal and distal chambers 28 and 30. A dual lumen tube is situated relative to the gas-permeable tubes such that an outer lumen terminates within the proximal chamber 28 and an inner lumen terminates within the distal chamber 30.

The Hattler patents disclose several embodiments of percutaneous oxygenators. In the simplest embodiment ('689), oxygen is circulated through a plurality of hollow, gas-permeable fibers forming loops inserted through a single incision into a blood vessel. In other embodiments ('809), the fiber loops are bisected and placed in fluid communication with a mixing chamber within a tip at the distal end of the device.

Tanishita, et al., disclose an extracorporeal oxygenator (FIGS. 1A and 1B) in which diffusion of gases was enhanced by application of pulsatile flow superimposed on a steady mean flow. Flow pulsation is introduced in the oxygenator chamber by directly vibrating its bottom plate.

3. Solution to the Problem

The problem of streaming appears not to have been recognized in prior art percutaneous oxygenators. None of the prior art references known to applicant shows a percutaneous oxygenator that can be inflated and deflated to minimize streaming, and thereby maximize cross-diffusion of gases between the patient's blood stream and the oxygenator.

SUMMARY OF THE INVENTION

This invention provides a percutaneous oxygenator having an inflatable balloon suitable for insertion into a blood vessel. Oxygen is circulated through a number of gas-permeable passageways (such as hollow gas-permeable fibers) adjacent to the balloon surface to permit diffusion of oxygen and carbon dioxide between the blood vessel and the passageways. A pump is used to alternately expand and contract the balloon. This causes movement of the passageways within the blood vessel to minimize streaming of the blood flow around the oxygenator, maximizes turbulence in the blood stream, and therefore maximizes cross-diffusion of gases between the oxygenator and the patient's bloodstream. An external connector has lumens that supply a flow of oxygen to the passageways, exhaust gas from the passageways, and allow inflation and deflation of the balloon by the pump.

A primary object of the present invention is to provide an oxygenator that minimizes the problem of streaming or channeling that has heretofore limited the effective rate of diffusion of gases in oxygenators.

Another object of the present invention is to provide an oxygenator that can be easily implanted into a patient through a single incision to effectively boost the oxygen level and to remove carbon dioxide from the patient's blood.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a side cross-sectional view of one embodiment of the present invention with the balloon inflated.

FIG. 2 is another cross-sectional view taken along plane 2—2 of FIG. 1.

FIG. 3 is yet another cross-sectional view taken along plane 3—3 of FIG. 1.

FIG. 4 is a side cross-sectional view corresponding to FIG. 1 in which the balloon has been deflated.

FIG. 5 is another cross-sectional view taken along plane 5—5 of FIG. 4.

DETAILED DESCRIPTION OF THE INVENTION

Figure 6:
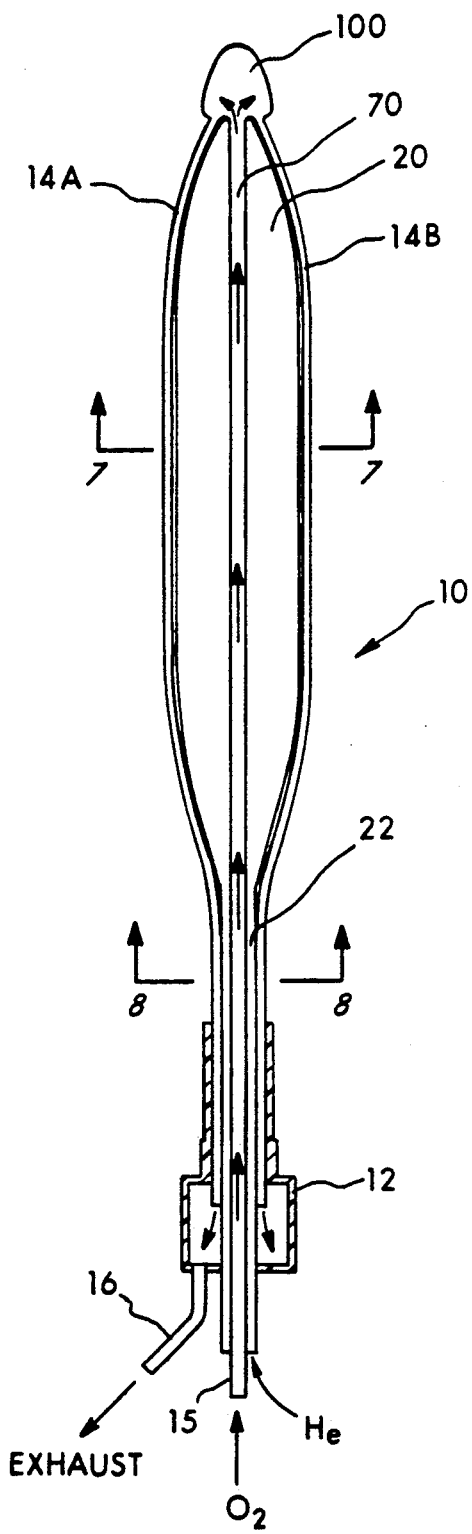
FIG. 6 is a side cross-sectional view of an alternative embodiment of the present invention having a central oxygen supply tube and a hollow tip member.

Turning to FIG. 1, a side cross-sectional view of the oxygenator 10 is shown. The major components are an inflatable balloon 20 and a number of gas passageways 14 which substantially surround the balloon 20. In the preferred embodiment, these gas passageways are a multitude of hollow gas-permeable fibers or tubules. The fibers 14 are formed into loops, as shown in FIGS. 1-3, that substantially surround and cover the exterior surface of balloon 20. The gas-permeable walls of the fibers 14 provide a large total surface area for diffusion of oxygen into the blood stream, and diffusion of carbon dioxide out of the blood stream. Any of a variety of flexible, hollow, gas-permeable fibers currently available on the market, such as Mitsubishi KPF190M polypropylene fibers, are suitable for this purpose. To provide a true ideal membrane, the polypropylene fibers should be coated with silicone rubber and bonded with a non-thrombogenic component.

The balloon 20 and fiber loops 14 of the device are implanted in the venous system of the patient through a single small incision. For example, the device 10 can be implanted through the right interior jugular vein into the superior vena cava of a patient. For maximum effectiveness, the balloon 20 and fiber loops 14 are fully inserted through the incision up to the level of the connector 12. Insertion of the balloon 20 and fiber loops 14 can be aided by using a conventional introducer similar to the type presently employed to insert a cardiac pacemaker.

The connector 12 provides separate lumens to supply and exhaust the fiber loops 14 and for inflation of the balloon 20. An external pump 21 is connected to the balloon inflation lumen 22 of the connector 12 and can be used to repeatedly inflate and deflate the balloon 20 at a predetermined frequency. A frequency of approximately forty cycles per minute has been experimentally demonstrated to provide satisfactory results in minimizing streaming and maintaining a turbulent flow of blood adjacent to the oxygenator. Any gas or fluid can be pumped into and released from the balloon for this purpose. However, helium offers the advantages of having very low viscosity and density for ease of pumping. Carbon dioxide as a gas offers safety features and is quickly dissolved in the bloodstream in the event of balloon leakage. In the preferred embodiment, at least a portion of the fiber loops 14 are secured to the exterior surface of the inflation balloon 20 (e.g. by adhesive bonding). This helps to insure that expansion and contraction of the balloon 20 causes movement of the fibers 14 within the blood vessel. FIGS. 1 and 2 provide cross-sectional views of the oxygenator 10 with the balloon 20 fully inflated. In comparison, FIGS. 4 and 5 show the same oxygenator with the balloon 20 deflated.

After the device has been implanted, a supply of oxygen-containing gas is connected to the second lumen 15 of the connector 12. The oxygen flows through second lumen 15 into the fiber loops 14. Oxygen flows along the interior passageways of the fibers 14 and diffuses outward through the gas-permeable walls of the fibers into the surrounding blood stream. Carbon dioxide also diffuses inward from the blood stream through these gas-permeable walls into the interior of the fibers. Carbon dioxide and any remaining oxygen in the fibers are vented to the atmosphere at the distal ends of the fibers through a third lumen 16 in the connector 12. Negative pressurization can be applied by means of a suction pump 19 connected to the third lumen 16 to enhance gas flow through the fiber loops.

It should be noted that the present invention can also be used to administer anesthetic gases or other medications directly into the patient's blood system. For this purpose, a mixture of oxygen and anesthetic gases flow through the fiber loops of the device and diffuse into the patient's blood stream.

Figure 7:
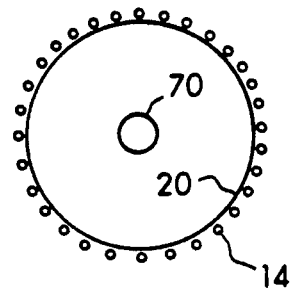
FIG. 7 is another cross-sectional view taken along plane 7—7 of FIG. 6.
Figure 8:
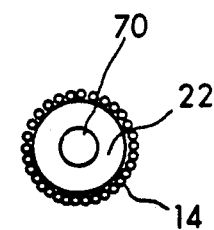
FIG. 8 is another cross-sectional view taken along plane 8—8 of FIG. 6.

FIGS. 6, 7, and 8 show an alternative embodiment of the oxygenator in which a hollow tip member 100 has been added at the distal end of the balloon 20. A central oxygen supply tube 70 extends through the connector 12 and the balloon 20 to the interior of the tip member 100. Each of the fiber loops is bisected at its distal point into two arms 14a and 14b. The resulting ends of the fibers are sealed in fluid communication with the internal cavity of the tip 100. The tip member 100 can be molded from plastic or rubber around the ends of the fibers to prevent the escape of gases at the junction between the fiber ends and the tip member 100. The tip can also be shaped with a tapered contour to ease insertion of the device through an incision. Thus, in this embodiment, oxygen-containing gases flow from an external supply through the oxygen supply tube 70, into the internal cavity of the tip member 100, through both arms 14a and 14b of the fibers, and are then exhausted through the exhaust lumen 16 in the connector 12, as previously described. It should be noted that the oxygen supply tube 70 and the balloon inflation lumen 22 can be formed as concentric tubes as shown in FIGS. 6 and 8. A cross-sectional view of the upper portion of the balloon 20 and the oxygen supply tube 70 is provided in FIG. 7. The oxygen supply tube 70 also acts as a structural support for the tip member 100 and fiber loops 14, and provides a degree of rigidity to aid initial insertion of the device into the blood vessel.

Figure 9:
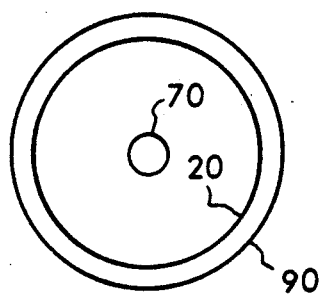
FIG. 9 is a cross-sectional view of an alternative embodiment in which the hollow fibers surrounding the inflation balloon are replaced with a single gas-permeable membrane.

FIG. 9 discloses another alternative embodiment in which the fibers 14 have been replaced by a single gas-permeable membrane 90 surrounding the inflation balloon 20. The resulting structure is essentially a balloon within a balloon. As before, oxygen-containing gas is supplied through the oxygen supply tube 70 to the tip member 100. The oxygen then flows from the tip member 100 back toward the connector 12 through the annular space between the inflation balloon 20 and the outer gas-permeable membrane 90. Cross-diffusion of oxygen and carbon dioxide occurs across the gas-permeable membrane between the annular space and the patient's bloodstream, as previously discussed. Repeated inflation and deflation of the inflation balloon 20 causes corresponding movements in the gas-permeable membrane 90 to minimize streaming. In yet another alternative embodiment, the gas-permeable membrane 90 can be tacked to the exterior surface of the inflation balloon 20 along a number of longitudinal lines to define a plurality of gas passageways extending from the tip member 100 to the connector 12.

Figure 10:
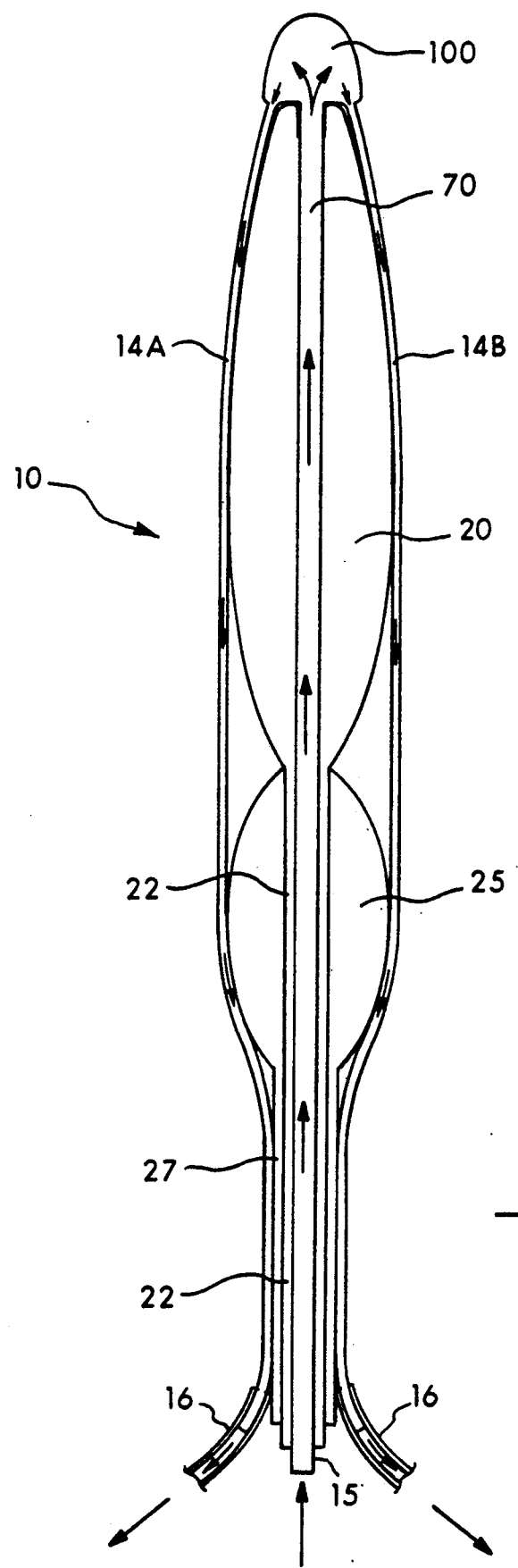
FIG. 10 is a cross-sectional view of yet another alternative embodiment in which two balloons are inflated and deflated asynchronously.

FIG. 10 shows yet another alternative embodiment of the present invention in which a second inflation balloon 25 has been added adjacent to the first inflation balloon 20. This second balloon 25 has a separate lumen 27 extending through the connector 12 to permit separate inflation and deflation of the second balloon 25 independent of the first balloon 20. In this embodiment, the balloons 20 and 25 will typically be inflated asynchronously (i.e., out of phase with one another) so that resulting turbulence in the patient's bloodstream is maximized.

The above disclosure sets forth a number of embodiments of the present invention. Other arrangements or embodiments, not precisely set forth, could be practiced under the teachings of the present invention and as set forth in the following claims.

I claim:

1. An inflatable percutaneous oxygenator comprising:
   an inflatable balloon for at least partial insertion through an incision into a blood vessel, having an exterior surface and an opening to permit selective expansion and contraction of said balloon by introducing gas into and removing gas from said balloon, respectively;
   a plurality of gas passageways adjacent to said balloon exterior surface, each gas passageway being formed at least in part by a hollow fiber having a gas permeable wall to permit diffusion of gases between said blood vessel and said gas passageway, whereby expansion and contraction of said balloon causes movement of at least a portion of said gas passageway within said blood vessel; and
   pump means to alternately expand and contract said balloon.

2. The oxygenator of claim 1, wherein at least a portion of said fibers are secured to the exterior surface of said inflation balloon.

3. The oxygenator of claim 1, further comprising connection means extending through said incision to said balloon opening, having lumens to supply a flow of gas to said gas passageways, to exhaust gas from said passageways, and to permit inflation and deflation of said balloon by said pump means.

4. The oxygenator of claim 3, wherein said connection means comprise a lumen to supply a flow of gas to said gas passageway at substantially ambient pressure, and suction means to exhaust gas from said gas passageway at negative pressure.

5. The oxygenator of claim 3, wherein said gas passageways comprise:
   a tip member distal from said connection means;
   a gas supply tube extending from said connection means to said tip member, adapted to deliver a supply of gas to said tip member; and
   a plurality of hollow, gas-permeable fibers, each fiber having a first end adapted to receive a flow of gas from said tip member and a second end adapted to exhaust said flow of gas to said connection means, said fibers substantially surrounding said inflation balloon.

6. The oxygenator of claim 5, wherein said gas supply tube extends from said connection means through said inflation balloon to said tip member.

7. The oxygenator of claim 3, wherein said gas passageways comprise:
   a first group of a number of hollow, gas-permeable fibers, each fiber having a first end adapted to receive a flow of gas from said connection means, and a second end;
   a tip member distal from said connection means having an interior cavity adapted to receive said flow of gas from said second ends of said first group of fibers; and
   a second group of a number of hollow, gas-permeable fibers, each fiber having a first end adapted to receive said flow of gas from said tip member, and a second end adapted to exhaust said flow of gas to said connection means, said first and second groups of fibers substantially surrounding said inflation balloon.

8. The oxygenator of claim 7, further comprising an elongated support member extending from said connection means supporting said tip member with respect to said connection means.

9. The oxygenator of claim 1, wherein said pump means repeatedly inflates and deflates said balloon at a predetermined frequency.

10. The oxygenator of claim 9, wherein said frequency is approximately forty cycles per minute.

11. The oxygenator of claim 9, further comprising at least one additional inflation balloon for at least partial insertion through said incision into said blood vessel and having an exterior surface adjacent to at least some of said gas passageways, said additional inflation balloon being repeatedly inflated and deflated asynchronously with said first inflation balloon.

12. The oxygenator of claim 1, wherein the gas within said balloon comprises helium.

13. An inflatable percutaneous oxygenator adapted to extend through a single incision in a patient into a blood vessel, said oxygenator comprising:

an inflatable balloon adapted for at least partial insertion into said blood vessel, having an exterior surface and an opening to permit selective expansion and contraction said balloon by introducing gas into and removing gas from said balloon, respectively;

pump means adapted to alternately expand and contract said balloon;

a plurality of gas-permeable, hollow fibers adapted to receive a flow of oxygen-containing gas, to permit diffusion of oxygen and carbon dioxide with blood in said blood vessel, and to exhaust said flow of gas; said fibers substantially surrounding at least a portion of said balloon surface so that expansion and contraction of said balloon causes movement of at least a portion of said fibers within said blood vessel; and an external connector extending through said incision into the patient to said balloon, having a first lumen to permit inflation and deflation of said balloon by said pump means, a second lumen to supply a flow of oxygen-containing gas to said fibers, and a third lumen to exhaust gas from said fibers.

14. The oxygenator of claim 13, wherein at least a portion of said fibers are secured to the exterior surface of said inflation balloon.

15. The oxygenator of claim 13, wherein each of said hollow fibers comprises a first end adapted to receive a flow of gas from said second lumen of said connector, and a second end adapted to exhaust gas to third lumen of said connector, with a loop of each fiber extending about a portion of said balloon within said blood vessel.

16. The oxygenator of claim 13, further comprising an elongated support member extending from said connector supporting said fibers with respect to said connector.

17. The oxygenator of claim 13, wherein said pump means repeatedly inflates and deflates said balloon at a predetermined frequency.

18. The oxygenator of claim 17, further comprising at least one additional inflation balloon for at least partial insertion through said incision into said blood vessel and having an exterior surface adjacent to at least some of said fibers, said additional inflation balloon being repeatedly inflated and deflated asynchronously with said first inflation balloon.

19. The oxygenator of claim 13, further comprising suction means attached to said third lumen of said connector to exhaust gas from said fibers at negative pressure.

20. An inflatable percutaneous oxygenator adapted to extend through a single incision in a patient into a blood vessel, said oxygenator comprising:

an inflatable balloon for at least partial insertion into said blood vessel, having an exterior surface permitting selective expansion and contraction of said balloon by introducing gas into and removing gas from said balloon, respectively;

an external connector extending through said incision into the patient adjacent to said balloon, having a balloon lumen to permit inflation and deflation of said balloon, and an exhaust lumen;

pump means connected to said balloon lumen of said connector to alternately expand and contract said balloon;

a tip member distal from said external connector;

a gas supply tube extending through said connector to said tip member to deliver a supply of oxygen-containing gas to said tip member; and a plurality of hollow, gas-permeable fibers, each fiber having a first end to receive a flow of oxygen-containing gas from said tip member and a second end to exhaust gas through said exhaust lumen of said connector, said fibers permitting diffusion of oxygen and carbon dioxide with blood in said blood vessel; said fibers substantially surrounding at least a portion of said balloon surface so that expansion and contraction of said balloon cause movement of at least a portion of said fibers within said blood vessel.

21. The oxygenator of claim 20, wherein said pump means repeatedly inflates and deflates said balloon at a predetermined frequency.

22. The oxygenator of claim 21, further comprising at least one additional balloon for at least partial insertion through said incision into said blood vessel and having an exterior surface adjacent to at least some of said fibers, said additional balloon being repeatedly inflated and deflated asynchronously with said first balloon.

23. The oxygenator of claim 20, wherein at least a portion of said fibers are secured to the exterior surface of said balloon.

24. The oxygenator of claim 20, further comprising suction means to exhaust gas from said exhaust lumen of said connector at negative pressure.

25. An inflatable percutaneous oxygenator adapted to extend through a single incision in a patient into a blood vessel, said oxygenator comprising:

an inflatable balloon for at least partial insertion into said blood vessel, having an exterior surface permitting selective expansion and contraction of said balloon by introducing gas into and removing gas from said balloon, respectively;

an external connector for insertion through said incision into the patient adjacent to said balloon, having a first lumen to permit inflation and deflation of said balloon, a second lumen to deliver a supply of oxygen-containing gas to said oxygenator, and a third lumen to exhaust gas from said oxygenator;

pump means connected to said first lumen of said connector to alternately expand and contract said balloon;

a first group of a number of hollow, gas-permeable fibers, each fiber having a first end to receive a flow of oxygen-containing gas from said second connector lumen, and a second end;

a tip member distal from said external connector having an interior cavity to receive said flow of gas from said second ends of said first group of fibers;

a second group of a number of hollow, gas-permeable fibers, each fiber having a first end to receive said flow of gas from said tip member, and a second end to exhaust said flow of gas through said third connector lumen, said first and second groups of fibers substantially surrounding at least a portion of said balloon.

26. The oxygenator of claim 25, wherein said pump means repeatedly inflates and deflates said balloon at a predetermined frequency.

27. The oxygenator of claim 26, further comprising at least one additional inflation balloon for at least partial insertion through said incision into said blood vessel and having an exterior surface adjacent to at least some of said fibers, said additional inflation balloon being repeatedly inflated and deflated asynchronously with said first balloon.

28. The oxygenator of claim 25, further comprising an elongated support member extending from said connector supporting said fibers with respect to said connector.

29. The oxygenator of claim 25, wherein at least a portion of said fibers are secured to the exterior surface of said balloon.

30. The oxygenator of claim 25, further comprising suction means operatively connected to said third connector lumen, adapted to exhaust gas from said second group of fibers at negative pressure.

* * * * *